United States Patent
Yadav et al.

(10) Patent No.: US 11,430,556 B2
(45) Date of Patent: Aug. 30, 2022

(54) MEDICATION MANAGEMENT PORTAL DEVICE, SYSTEM AND METHODS

(71) Applicants: Daven Raymond Yadav, Atlanta, GA (US); Anup Surendra Bottu, Atlanta, GA (US); Daniel Scott Burnham, Atlanta, GA (US); Van Alexander Panter, Marietta, GA (US)

(72) Inventors: Daven Raymond Yadav, Atlanta, GA (US); Anup Surendra Bottu, Atlanta, GA (US); Daniel Scott Burnham, Atlanta, GA (US); Van Alexander Panter, Marietta, GA (US)

(*) Notice: Subject to any disclaimer, the term of this patent is extended or adjusted under 35 U.S.C. 154(b) by 177 days.

(21) Appl. No.: 16/411,943

(22) Filed: May 14, 2019

(65) Prior Publication Data
US 2020/0051680 A1  Feb. 13, 2020

(51) Int. Cl.
| | | |
|---|---|---|
| *G06Q 10/00* | (2012.01) | |
| *G16H 20/13* | (2018.01) | |
| *G07C 9/00* | (2020.01) | |
| *H04N 7/18* | (2006.01) | |
| *G08B 21/18* | (2006.01) | |
| *G16H 80/00* | (2018.01) | |
| *H04N 7/14* | (2006.01) | |

(52) U.S. Cl.
CPC ......... *G16H 20/13* (2018.01); *G07C 9/00309* (2013.01); *G08B 21/182* (2013.01); *G16H 80/00* (2018.01); *H04N 7/183* (2013.01); *H04N 7/141* (2013.01)

(58) Field of Classification Search
CPC .... G16H 20/13; G16H 80/00; G07C 9/00309; G08B 21/182; H04N 7/183; H04N 7/141
USPC ............................................................. 705/2
See application file for complete search history.

(56) References Cited

U.S. PATENT DOCUMENTS

| | | | |
|---|---|---|---|
| 4,695,954 A | 9/1987 | Rose et al. | |
| 8,878,654 B2* | 11/2014 | Cohen-Alloro | G16H 20/13 340/572.1 |
| 9,400,873 B2* | 7/2016 | Kamen | G06Q 50/22 |
| 10,653,583 B1* | 5/2020 | Walker | A61J 7/0427 |
| 10,937,533 B1* | 3/2021 | Wiser | A61J 7/04 |
| 2002/0022973 A1* | 2/2002 | Sun | G16H 40/67 705/3 |
| 2002/0027507 A1* | 3/2002 | Yarin | G16H 20/13 705/2 |
| 2003/0086338 A1* | 5/2003 | Sastry | G16H 20/13 368/10 |
| 2005/0188853 A1* | 9/2005 | Scannell | F21V 33/00 96/417 |
| 2008/0316045 A1* | 12/2008 | Sriharto | G16H 40/20 700/214 |
| 2009/0222539 A1* | 9/2009 | Lewis | G16H 10/60 709/221 |

(Continued)

OTHER PUBLICATIONS

International Search report and Written opinion issued for Application No. PCT/US2020/032851, dated Jul. 27, 2020.

(Continued)

*Primary Examiner* — Zhen Y Wu
(74) *Attorney, Agent, or Firm* — Meunier Carlin & Curfman LLC

(57) ABSTRACT

The present disclosure relates to a medication management portal device, and techniques for managing a person's healthcare needs using the disclosed medication management portal device.

25 Claims, 15 Drawing Sheets

(56) References Cited

U.S. PATENT DOCUMENTS

| | | | |
|---|---|---|---|
| 2010/0314282 A1* | 12/2010 | Bowers | A61J 7/04 340/815.4 |
| 2012/0313785 A1* | 12/2012 | Hanson | G08B 23/00 340/573.1 |
| 2013/0002795 A1* | 1/2013 | Shavelsky | A61J 7/04 700/244 |
| 2014/0156296 A1* | 6/2014 | Stenzler | G16H 20/10 705/2 |
| 2015/0048100 A1* | 2/2015 | Dickie | G16H 40/60 221/1 |
| 2015/0186615 A1 | 7/2015 | Armor et al. | |
| 2016/0147976 A1* | 5/2016 | Jain | G16H 20/10 705/2 |
| 2016/0203292 A1 | 7/2016 | Kamen et al. | |
| 2017/0087059 A1* | 3/2017 | Rodriguez | A61J 7/0427 |
| 2017/0164892 A1* | 6/2017 | Sezan | G16H 20/13 |
| 2017/0193189 A1* | 7/2017 | Turnell | A61J 7/0427 |
| 2018/0000692 A1* | 1/2018 | Born | A61J 7/0436 |
| 2018/0068086 A1 | 3/2018 | Hanson et al. | |
| 2018/0160073 A1 | 6/2018 | Hyde et al. | |
| 2018/0174674 A1* | 6/2018 | Turnell | G16H 20/13 |
| 2018/0235843 A1* | 8/2018 | Latorraca | E05B 65/46 |
| 2019/0224077 A1* | 7/2019 | Stein | A61J 7/0076 |
| 2019/0267125 A1* | 8/2019 | Benzel | G16H 20/10 |
| 2019/0306303 A1* | 10/2019 | Daoud | H04M 1/72457 |
| 2019/0307647 A1* | 10/2019 | Greenspan | A61J 7/0076 |
| 2019/0365606 A1* | 12/2019 | Nezamuddin | A61J 7/04 |
| 2020/0179230 A1* | 6/2020 | Molloy | G16H 20/13 |

OTHER PUBLICATIONS

International Preliminary reporton Patentability issued for Application No. PCT/US2020/032851, dated Nov. 25, 2021.

Osterberg L., Blaschke T. 'Adherence to medication.' New England Journal of Medicine. 2005; 353(5); 487-497.

* cited by examiner

```
┌─────────────────────────────────────────────────────────────────────────┐
│ Providing a medication management portal device that has a camera in   │
│ communication with the processor of the medication management portal    │
│ device                                                                  │
│                               1002                                      │
└─────────────────────────────────────────────────────────────────────────┘
                                    │
┌─────────────────────────────────────────────────────────────────────────┐
│ Providing an alert by the medication management portal device that it  │
│ is a time for a patient to receive medication from one of the           │
│ receptacles of the medication management portal device                  │
│                               1004                                      │
└─────────────────────────────────────────────────────────────────────────┘
                                    │
┌─────────────────────────────────────────────────────────────────────────┐
│ Providing an indication by the medication management portal device     │
│ that allows the user to identify the receptacle that the medication is  │
│ to be retrieved from                                                    │
│                               1006                                      │
└─────────────────────────────────────────────────────────────────────────┘
                                    │
┌─────────────────────────────────────────────────────────────────────────┐
│ The medication management portal device causes the camera to begin     │
│ recording the user retrieving the medication from the identified        │
│ receptacle and also records the user or a patient using the medication  │
│ from the identified receptacle                                          │
│                               1008                                      │
└─────────────────────────────────────────────────────────────────────────┘
                                    │
┌─────────────────────────────────────────────────────────────────────────┐
│ Video of the user retrieving the medication from the identified        │
│ receptacle and the user or the patient using the medication from the    │
│ identified receptacle is transmitted (real-time or delayed) over the    │
│ network to a device under the control of a health care professional     │
│                               1010                                      │
└─────────────────────────────────────────────────────────────────────────┘
                                    │
┌─────────────────────────────────────────────────────────────────────────┐
│ The video is used to verify that the user's or the patient' use of the │
│ medication from the identified receptacle is or is not in compliance    │
│ to the medication regimen                                               │
│                               1012                                      │
└─────────────────────────────────────────────────────────────────────────┘
```

FIG. 10

Providing a medication management portal device having a plurality of medication receptacles
1102

The medication management portal device receives information via an I/O device for a medication that is placed in one of the receptacles, wherein the medication information may include a medication identifier for the medication placed in the one of the receptacles
1104

The medication management portal device associates the medication identifier with a unique receptacle identifier for the receptacle that the medication is placed in.
1106

The medication management portal device receives information via the I/O device indicating one or more days or times during a day that a patient is to access the medication in the one of the receptacles
1108

The medication management portal device provides an indication using an indicator associated with the one of the plurality of the receptacles when it is the one or more days or times during a day that a patient is to access the medication in the one of the receptacles.
1110

FIG. 11

Providing a medication management portal device having a plurality of medication receptacles that includes one or more physiological monitoring devices in communication with a processor of the medication management portal device that are used to measure one or more of ECG, respiration, heart rate, temperature, blood pressure urinalysis, and stool analysis information
1202

The medication management portal device transmits information from one or more of the physiological monitoring devices, the information obtained from one or more of the physiological devices is obtained at or near a time that a user retrieves a medication from one of the receptacles of the medication management portal device, over a network connected to the medication management portal device to a device configured to store information
1204

The medication management portal device transmits over the network to the device configured to store information, a medication identifier for the medication that the user retrieved from the one of the receptacles of the medication management portal device
1206

The medication management portal device transmits over the network to the device configured to store information, patient information that is entered into the medication management portal device using the I/O device, wherein the patient information includes one or more of age, weight, race, sex, ethnicity, and genotype
1208

The information from one or more of the physiological monitoring devices, the medication identifier for the medication that the user retrieved from the one of the receptacles of the medication management portal device, and the patient information is associated and archived in the device configured to store information
1210

The stored information is used for medical analyses and/or studies
1212

FIG. 12

MEDICATION MANAGEMENT PORTAL DEVICE, SYSTEM AND METHODS

TECHNICAL FIELD

The present disclosure relates to a medication management portal for ensuring medication compliance and providing remote medical connection.

BACKGROUND

It has been estimated that up to 125,000 American deaths annually are the result of medication errors because taking medications is complicated and confusing. Medication errors include improper adherence to prescribed dosage, taking the wrong medication, not taking their medication or not taking their medication at the proper time, taking their medication improperly in combination with other medications, drugs or alcohol, and the like.

Approximately 41 percent of patients over the age 65 are on multiple medications (5-8 medications). Polypharmacy leads to non-adherence; it is estimated that over 35% of elderly who were taking four or more medications were non-adherent to their medication regimen. Non-adherence is associated with disease progression, treatment failure, hospitalizations and other adverse drug events (ADEs). Non-adherence can lead to a number of very serious health consequences. It is estimated that 4.3 million health care visits annually are due to ADE and 40 percent of elderly patients experience an ADE. In 2012, 2.6 million hospitalizations were related to medication errors. Not only does the difficulty of taking medications properly cause suffering for patients and their families, the financial burden on the U.S. economy is enormous. It is estimated that medication non-adherence results in $317 billion in additional healthcare costs every year. The cost to a single patient can be quite high, for example non-adherence can increase the cost to a diabetic patient by over $5,000 in a single year.

The conventional mainstay to help patients take their medications properly are mechanical pill boxes that are confusing and difficult to use. Loading these mechanical with pills is particularly difficult and frustrating Further, the mechanical boxes are "dumb"—they don't provide any reminders to take your medications and don't let your family members or care providers know if you have not taken your medications.

Dr. Osterberg, one of the leading researchers into medication non-adherence, writing in the New England Journal of Medicine, suggested the development of smart phones and smart pill boxes to solve this difficult problem: "New technologies such as reminders through cell phones and personal digital assistants and pillboxes with paging systems may be needed to help patients who have the most difficulty meeting the goals of a complex medication regimen." (Osterberg L., Blaschke T. 'Adherence to medication.' New England Journal of Medicine. 2005; 353(5); 487-497.)

The present disclosure is directed to overcoming these and other challenges. While several examples of challenges that arise in a medication management are described, other problems and solutions are discussed below throughout the specification, and the scope of the claims should not be limited to addressing only challenges associated with medication management.

SUMMARY

Described in this disclosure are systems and methods for medication management. For example, one embodiment of the system is comprised of a plurality of receptacles, each configured to receive and hold a medication; an indicator associated with each of the plurality of receptacles; a processor communicatively coupled to each of the indicators; a memory in communication with the processor; a communications interface coupled with the processor for connecting the medication management system to a network; a display in communication with the processor; an input-output (IO) device in communication with the processor, wherein the processor executes computer-executable instructions to track dates and time, and wherein the processor further executes computer-executable instructions that cause the processor to: individually identify each of the plurality of receptacles, wherein each of the plurality of receptacles has a unique receptacle identifier; receive information via the I/O device if a medication is placed in one of the receptacles; receive a medication identifier for the medication placed in the one of the receptacles; associate the medication identifier with the unique receptacle identifier for the receptacle that the medication is placed in; receive information via the I/O device indicating one or more days or times during a day that a patient is to access the medication in the one of the receptacles; and provide an indication using the indicator associated with the one of the plurality of the receptacles when it is the one or more days or times during a day that a patient is to access the medication in the one of the receptacles.

One embodiment of a method of medication management comprises providing a medication management device, wherein the medication management portal device is comprised of: a plurality of receptacles, each configured to receive and hold a medication; an indicator associated with each of the plurality of receptacles; a processor communicatively coupled to each of the indicators, wherein the processor executes computer-executable instructions to track dates and time, and wherein the processor further executes computer-executable instructions that cause the processor to individually identify each of the plurality of receptacles, wherein each of the plurality of receptacles has a unique receptacle identifier; a memory in communication with the processor; a communications interface coupled with the processor for connecting the medication management system to a network; a display in communication with the processor; and an input-output (I/O) device in communication with the processor; receiving, by the medication management device, information via the I/O device for a medication is placed in one of the receptacles; receiving, by the medication management device, a medication identifier for the medication placed in the one of the receptacles; associating, by the medication management device, the medication identifier with the unique receptacle identifier for the receptacle that the medication is placed in; receiving, by the medication management device, information via the I/O device indicating one or more days or times during a day that a patient is to access the medication in the one of the receptacles; and providing, by the medication management device, an indication using the indicator associated with the one of the plurality of the receptacles when it is the one or more days or times during a day that a patient is to access the medication in the one of the receptacles.

Another embodiment of a method comprises a method of verifying adherence to a medication regimen using a medication management device. The method comprises providing a medication management device, wherein the medication management portal device is comprised of: a plurality of receptacles, each configured to receive and hold a medication; an indicator associated with each of the plurality of receptacles; a processor communicatively coupled to each of the indicators, wherein the processor executes computer-executable instructions to track dates and time, and wherein the processor further executes computer-executable instructions that cause the processor to individually identify each of the plurality of receptacles, wherein each of the plurality of receptacles has a unique receptacle identifier; a memory in communication with the processor; a communications interface coupled with the processor that connects the medication management system to a network; a display in communication with the processor; an input-output (I/O) device in communication with the processor; and a camera in communication with the processor; providing, by the medication management device, an alert that it is a time for a patient to receive medication from one of the receptacles of the medication management device; providing, by the medication management device, an indication that allows the user to identify the receptacle that the medication is to be retrieved from; recording, by the medication management device, using the camera, a user retrieving the medication from the identified receptacle; recording, by the medication management device, using the camera, the user or a patient using the medication from the identified receptacle; and transmitting, by the medication management device, a video of the user retrieving the medication from the identified receptacle and the user or the patient using the medication from the identified receptacle, wherein the video is transmitted over the network to a device under the control of a health care professional.

Yet another embodiment of a disclosed method comprises a method of collecting medical information using a medication management device. The method comprises providing a medication management device, wherein the medication management portal device is comprised of: a plurality of receptacles, each configured to receive and hold a medication; an indicator associated with each of the plurality of receptacles; a processor communicatively coupled to each of the indicators, wherein the processor executes computer-executable instructions to track dates and time, and wherein the processor further executes computer-executable instructions that cause the processor to individually identify each of the plurality of receptacles, wherein each of the plurality of receptacles has a unique receptacle identifier; a memory in communication with the processor; a communications interface coupled with the processor that connects the medication management system to a network; a display in communication with the processor; an input-output (I/O) device in communication with the processor; and one or more physiological monitoring devices that are used to measure one or more of ECG, respiration, heart rate, temperature, blood pressure urinalysis, and stool analysis information in communication with the processor; transmitting, by the medication management device, information from one or more of the physiological monitoring devices, wherein the information from one or more of the physiological devices is obtained at or near a time that a user retrieves a medication from one of the receptacles of the medication management device, wherein the information is transmitted over the network to a device configured to store information; transmitting, by the medication management device, over the network to the device configured to store information, a medication identifier for the medication that the user retrieved from the one of the receptacles of the medication management device; and transmitting, by the medication management device, over the network to the device configured to store information, patient information that is entered into the medication management portal device using the I/O device, wherein the patient information includes one or more of age, weight, race, sex, ethnicity, and genotype.

Other systems, methods, features and/or advantages will become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The accompanying drawings, which are incorporated in and constitute a part of this specification, illustrate embodiments and together with the description, serve to explain the principles of the methods and systems:

FIG. 10 is a flowchart illustrating a method of performing a method of verifying adherence to a medication regimen using a medication management portal device.

FIG. 11 is a flowchart illustrating a method of medication management.

FIG. 12 is a flowchart that illustrates a method of collecting medical information using a medication management portal device.

DETAILED DESCRIPTION

The present disclosure relates to a medication management portal device and techniques for managing healthcare using the medication management portal device.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬ from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

Figure 1:
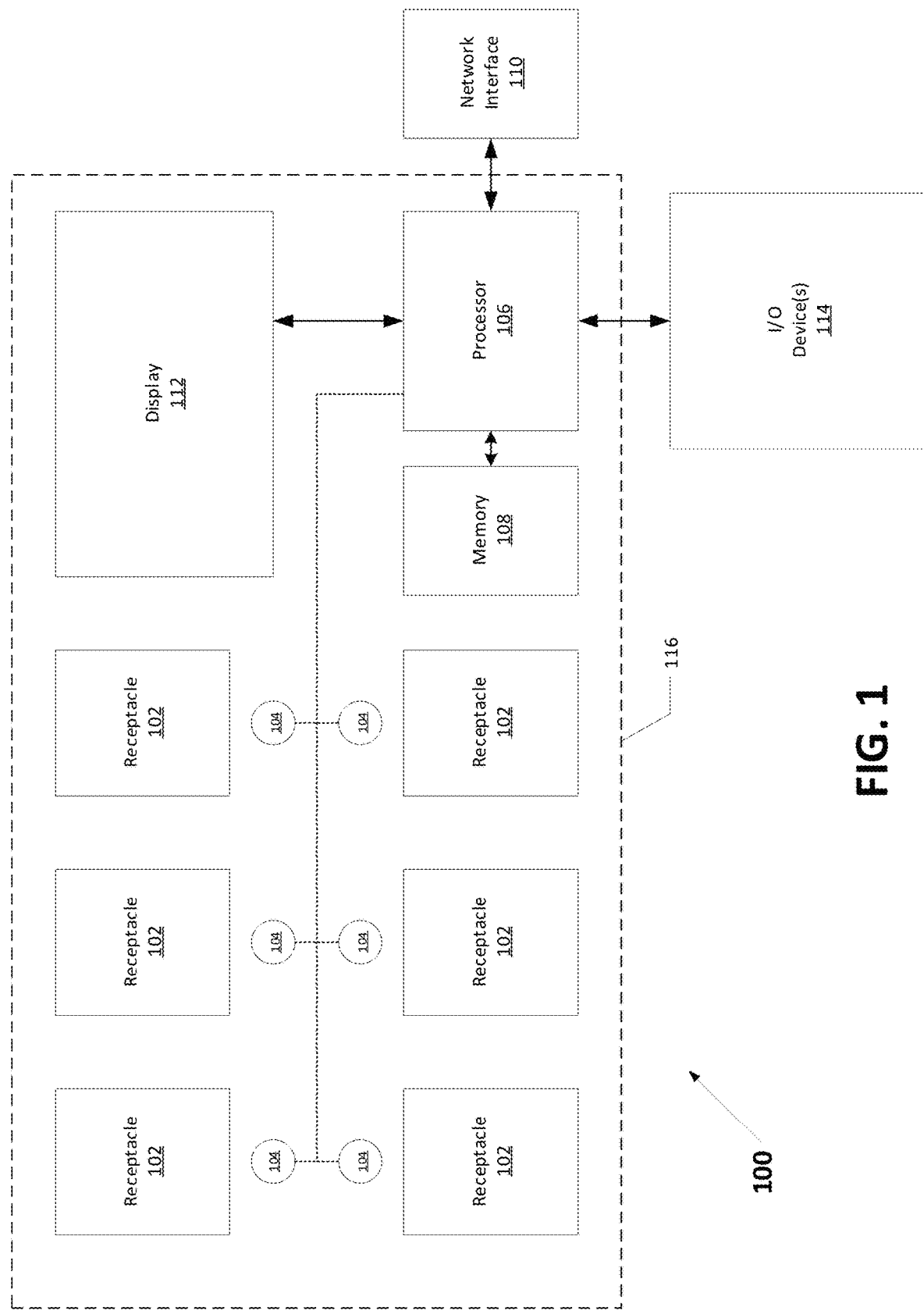
FIG. 1 illustrates an exemplary medication management portal device.

FIG. 1 illustrates an exemplary medication management portal device 100. The embodiment illustrated in FIG. 1 is comprised of a plurality of receptacles 102, where each receptacle 102 is configured to receive and hold a medication. An indicator 104 is associated with each of the plurality of receptacles 102. Generally, the indicator 104 provides an indication (e.g., alarm) associated with the one of the plurality of the receptacles 102 when it is the one or more days or times during a day that a patient is to access the medication in the one of the receptacles 102. The indicator 104 may be in various forms. For example, at least one of the indicators 104 associated with each of the plurality of receptacles 102 may comprise a light (e.g., a LED) located proximate to the at least one receptacle 102. Alternatively or optionally, at least one of the indicators 104 associated with each of the plurality of receptacles 102 may comprise a sound-emitting device located proximate to the at least one receptacle. Alternatively or optionally, at least one of the indicators 104 associated with each of the plurality of receptacles 102 comprises a haptic vibration device located proximate to the at least one receptacle 102. Generally, the indicator 104 may be any device that can provide an alarm or indication to a person. The indicator 104 is controlled by a processor (further described below) executing computer-executable instructions such that the indicator 104 provides an indication (e.g., emits light, sound, vibration, etc.) when the alarm is triggered.

Further comprising the embodiment of the medication management portal device 100 of FIG. 1 is a processor 106 communicatively coupled to each of the indicators 104, a memory 108 in communication with the processor 106, and a communications interface 110 coupled with the processor 106 for connecting the medication management portal device 100 to a network (not shown in FIG. 1). The medication management portal device 100 further comprises a display 112 in communication with the processor 106, and an input-output (I/O) device 114 in communication with the processor 106. The processor 106 executes computer-executable instructions to at least track dates and time and perform other functions. Generally, these computer-executable instructions are stored in the memory 108. The computer-executable instructions, in addition to tracking dates and times, cause the processor 106 to individually identify each of the plurality of receptacles 102 by assigning each of the plurality of receptacles 102 a unique receptacle identifier (which also may be stored in the memory 108); receive information via the I/O device 114 if a medication is placed in one of the receptacles 102; receive a medication identifier for the medication placed in the one of the receptacles 102; associate the medication identifier with the unique receptacle identifier for the receptacle 102 that the medication is placed in; receive information via the I/O device 114 indicating one or more days or times during a day that a patient is to access the medication in the one of the receptacles 102; and provide an indication using the indicator 104 associated with the one of the plurality of the receptacles 102 when it is the one or more days or times during a day that a patient is to access the medication in the one of the receptacles 102. In some instances, the processor 106 executes computer-executable instructions to display a calendar on the display 112, wherein the calendar displays the one or more days or times during a day that a patient is to access the medication in the one of the receptacles 102.

Optionally, the receptacles 102 and some of the other components (e.g., processor 106, memory 108, display 112, etc.) of the medication management portal device 100 may be contained in an enclosure 116. The enclosure 116 may be made of metal, wood, plastic, or any other suitable material, or combinations thereof.

In some instances, information about the medication placed in the one of the receptacles 102 is displayed on the display 112 when the processor 106 receives the medication identifier. The information about the medication placed in the one of the receptacles 102 may be stored in the memory 108 by the processor 106 and retrieved from the memory 108 by the processor 106 using the medication identifier. As noted above, the medication management portal device 100 may be connected to a network, and in some instances, the information about the medication placed in the one of the receptacles 102 may be at least partially retrieved over the network by the processor 106 using the medication identifier and displayed on the display 112. In some instances, the display 112 can be used to display a plurality of medication identifiers and the medication identifier for the medication placed in the one of the receptacles 102 can be selected from among the plurality of medication identifiers using the I/O device 114. Also, in some instances, the medication identifier may be input into the medication management portal device 100 and stored in the memory 108 using the I/O device 114. For example, the I/O device 114 may comprise a keyboard, and the medication identifier is input into the medication management portal device 100 using the keyboard. Optionally or alternatively, the I/O device 114 may comprise a scanner, and the scanner may be used to scan the medication or information associated with the medication and the processor 106 executes computer-executable instructions to determine the medication identifier from the scanned information.

Figure 2B:
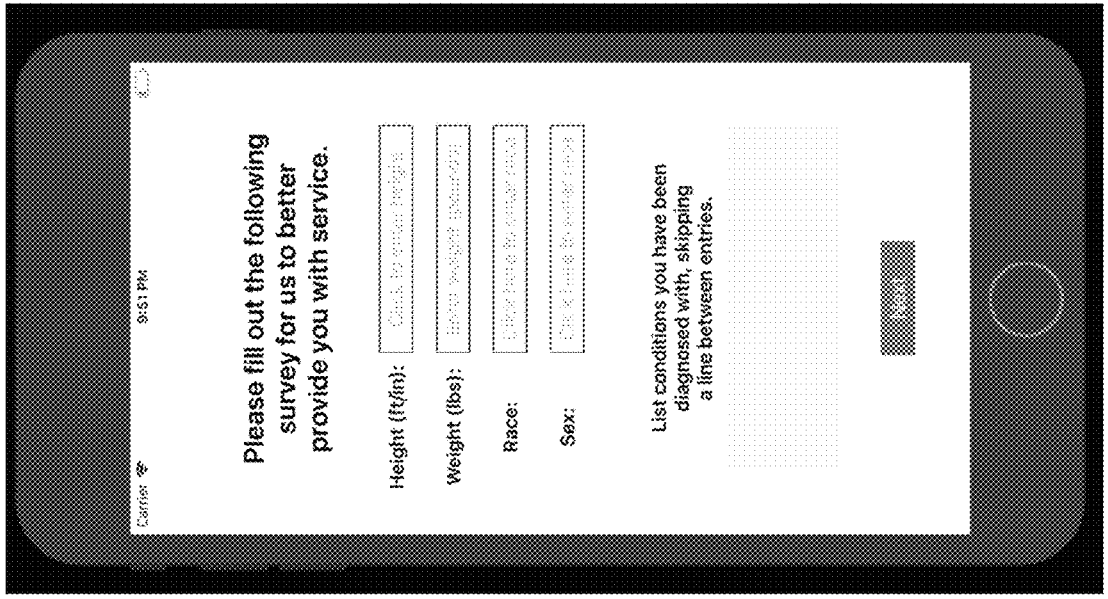
FIGS. 2A-2G are exemplary screen shots of graphical user interfaces used to access and enter data into an embodiment of a medication management portal device.
Figure 2A:
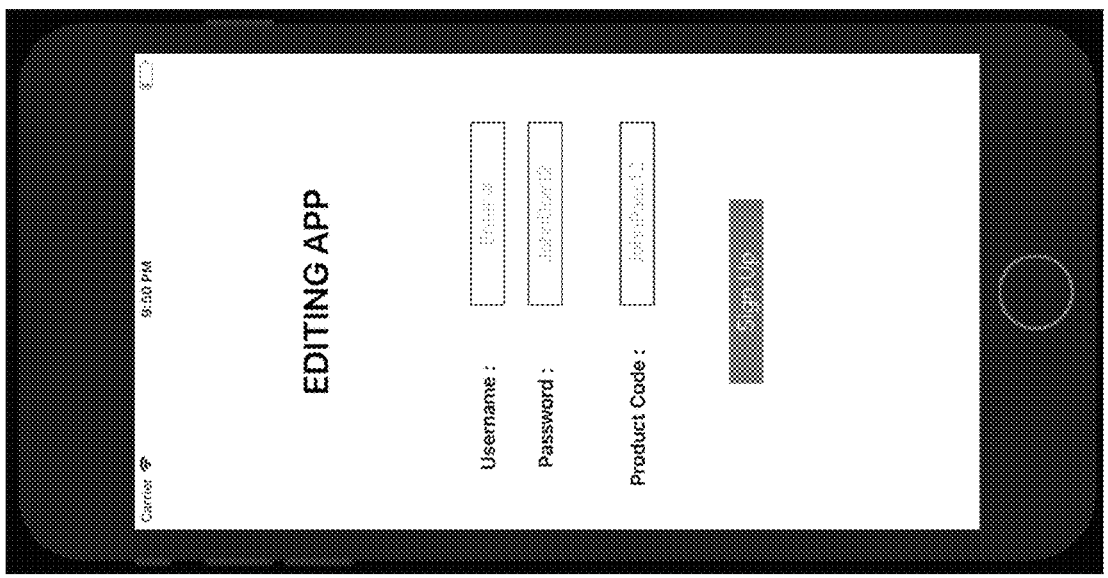
Figure 2D:
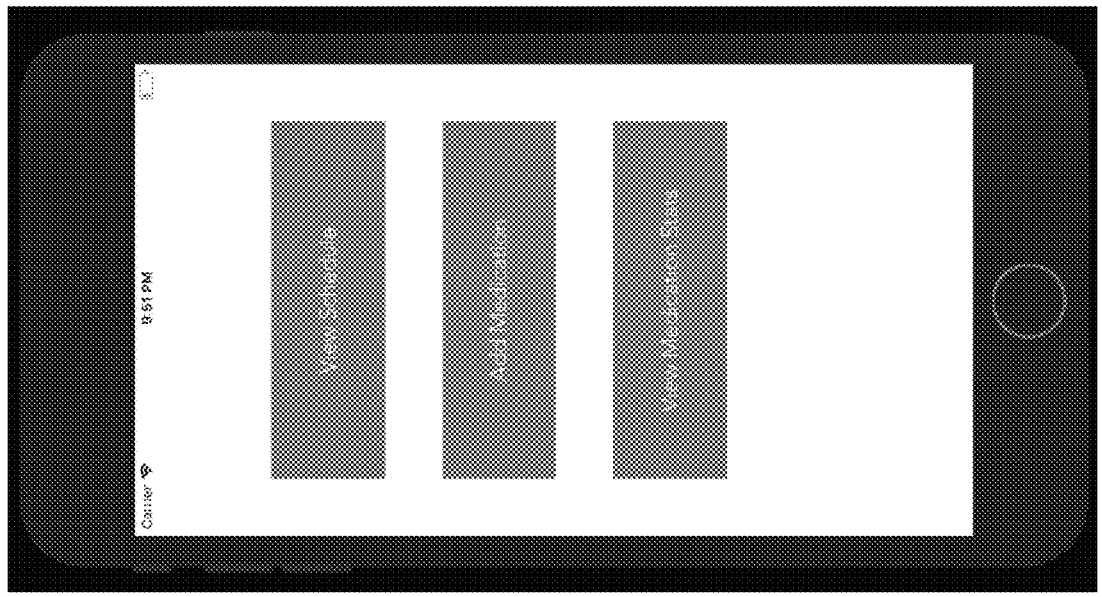
Figure 2C:
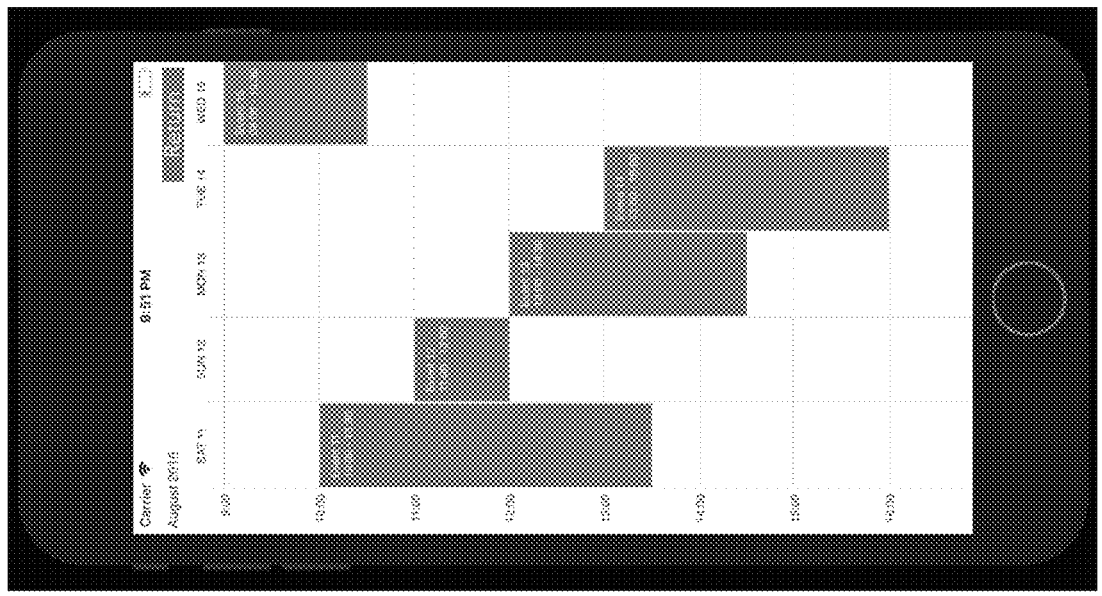
Figure 2F:
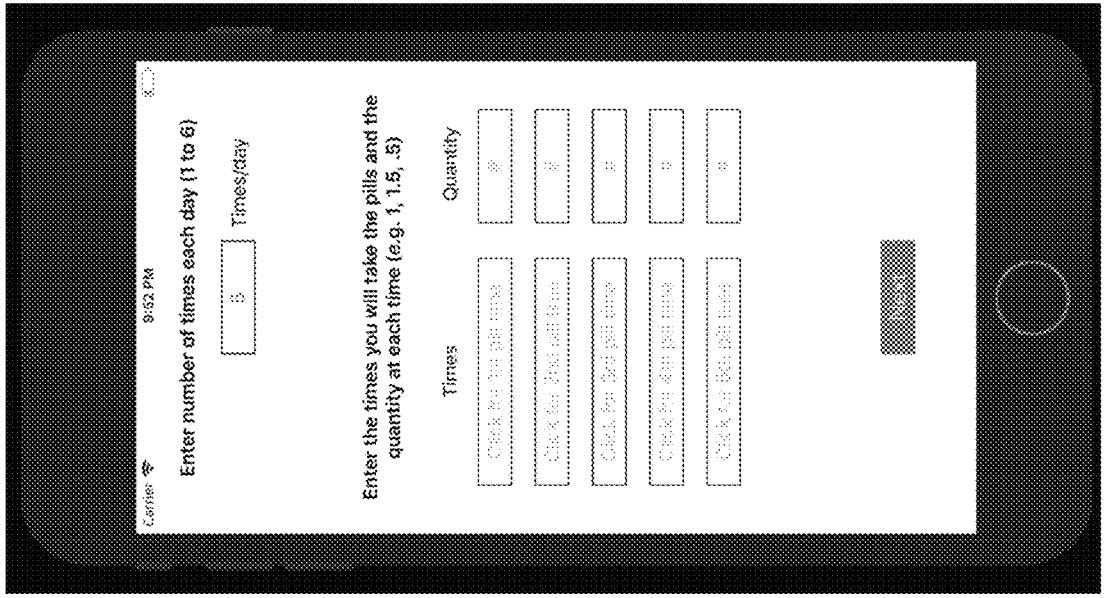
Figure 2E:
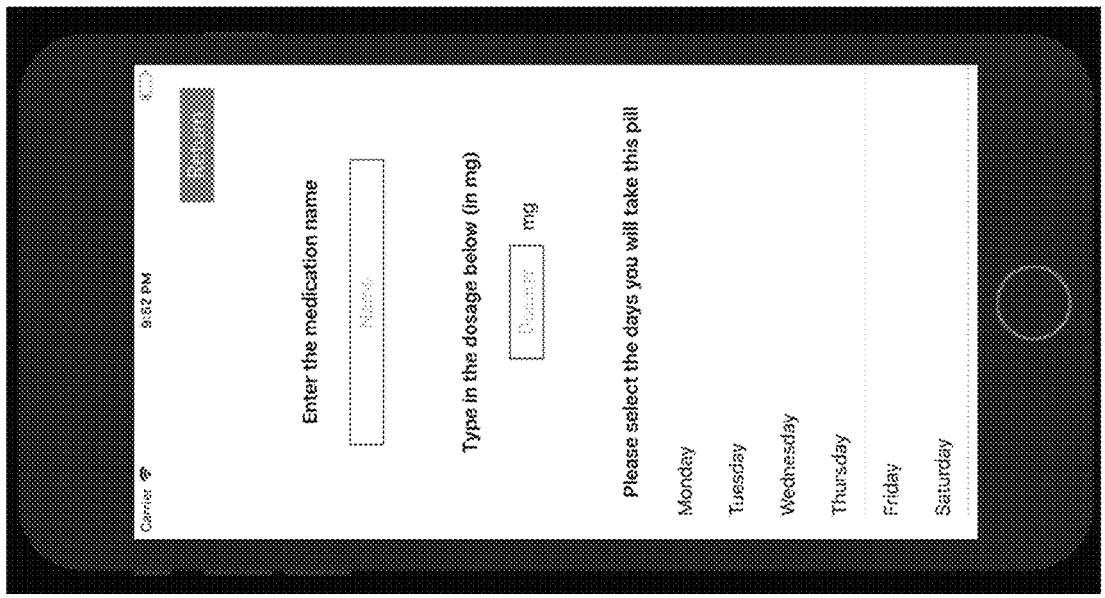
Figure 2G:
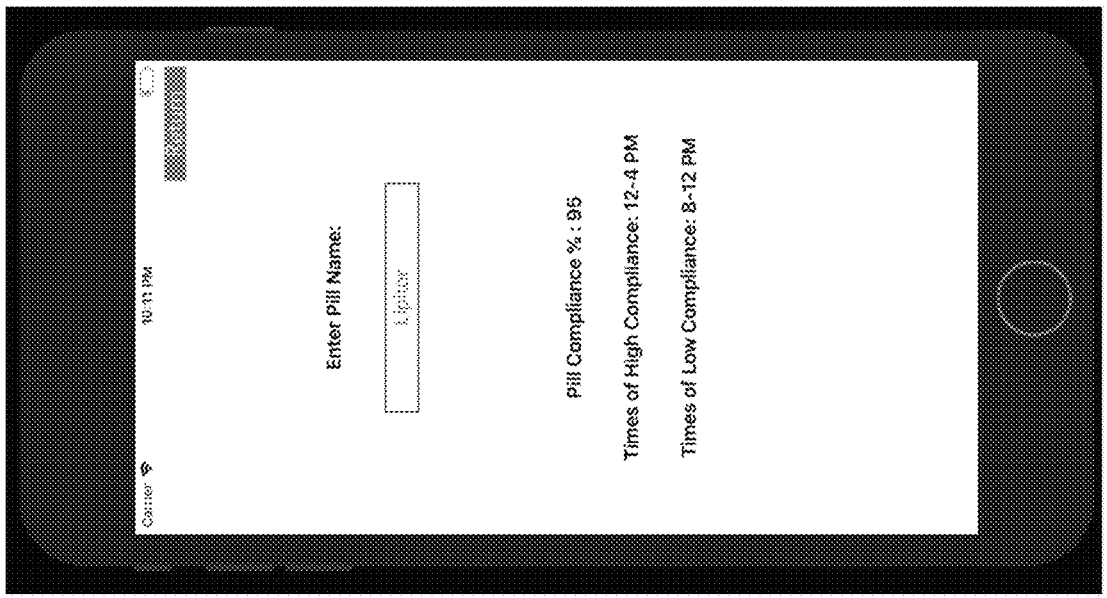

As shown in FIG. 1, the medication management portal device 100 includes a communications interface 110. For example, the communications interface 110 may comprise a wireless communications interface that wirelessly connects the medication management portal device 100 to the network. For example, the network may at least in part comprise a WLAN with internet access. Alternatively or optionally, the communications interface 110 may comprise a wired communications interface that connects the medication management system to the network (e.g. LAN with internet access). The network may be connected to a cellular phone system, such that a user may interface with the medication management portal device for entering information and/or accessing the device 100. For example, FIGS. 2A-2G are exemplary screen shots of graphical user interfaces (GUIs) used to access and enter data into an embodiment of a medication management portal device 100. These GUIs may be displayed on the display 112 and information entered using the I/O device 114, and/or the GUIs may be displayed on a display of a smartphone that is used to access the medication management portal device 100 over the network. It is to be appreciated that these GUIs are only examples and other GUIs that vary in appearance and/or information requested are contemplated within the scope of this disclosure. FIG. 2A shows the log in GUI; FIG. 2B shows the GUI for demographic information; FIG. 2C shows the medication schedule in a calendar format; FIG. 2D is the GUI for navigating through the functions of the application; FIG. 2E is the GUI for entering a new medication; FIG. 2F is the GUI for adding details for a new medication; FIG. 2G is the GUI for obtaining compliance information on a medication.

Figure 3:
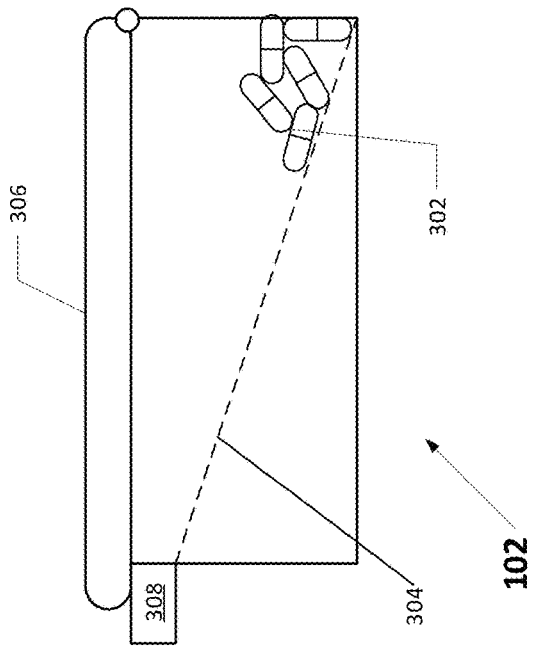
FIG. 3 illustrates an alternate exemplary medication management portal device.
Figure 4:
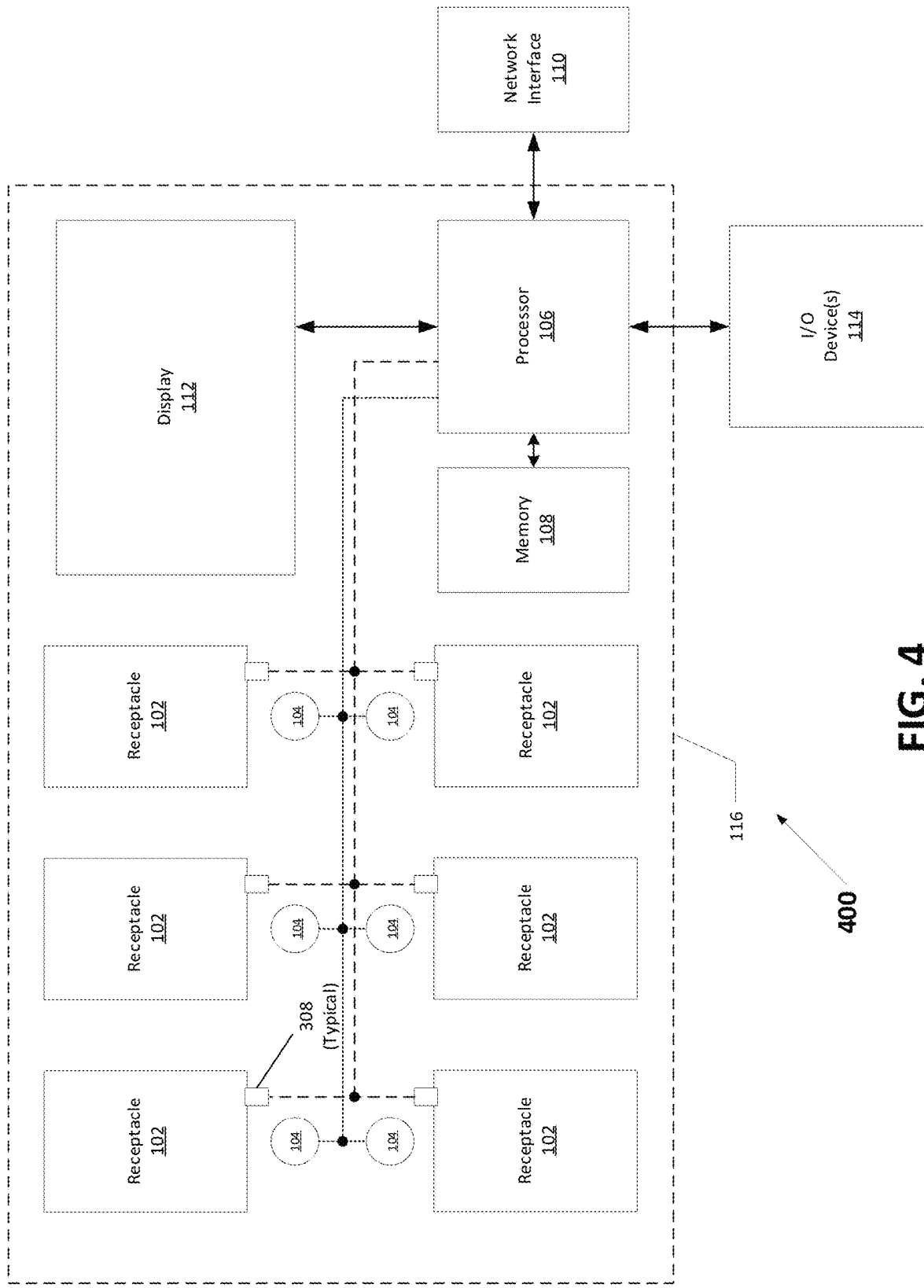
FIG. 4 illustrates yet another alternate exemplary medication management portal device.

As noted herein, the receptacles 102 are configured to hold medications. FIG. 3 illustrates a side view of an exemplary single receptacle 102 of an embodiment of an medication management portal device that is configured to hold a medication in a pill form 302. In FIG. 3, the receptacle 102 has a sloped bottom 304 that not only helps contain the pills 302 in the receptacle 102, but also facilitates removal of the pill(s) 302 from the receptacle 102 as they can be slid along the bottom 304 of the receptacle 102 until reaching the lip where the pill(s) 302 can be more easily grasped. The receptacle 102 shown in FIG. 3 has an individual lid 306, which may or may not have a timed lock that is connected to the processor 106. The embodiment of a receptacle 102 of FIG. 3 also has an optional sensor 308 that detects a presence or absence of an object in the at least one receptacle 102. For example, the sensor 308 may detect the presence or absence of the medication 302 in the at least one receptacle 102. The sensor 308 may also be used to detect retrieval of at least a portion of the medication 302 in the at least one receptacle 102. The sensor 308 is in communication with the processor 106, so the processor 106 may be used to record a time and date in the memory 108 that at least a portion of the medication 302 was retrieved from the receptacle 102. In one non-limiting example, the sensor 308 comprises an infrared (IR) sensor. FIG. 4 is an illustration of an alternate embodiment of a medication management portal device 400 wherein each of the one or more receptacles has an associated sensor 308.

While one or more of the receptacles 102 may be configured to hold medication in a pill form 302, one or more other receptacles 102 may be configured to hold a medication in a liquid form, to hold a medication in a pre-packaged form, or to hold medications in any form that they are provided to a patient. For example, the pre-packaged medication may be in a tear-off strip or roll form.

Figure 5:
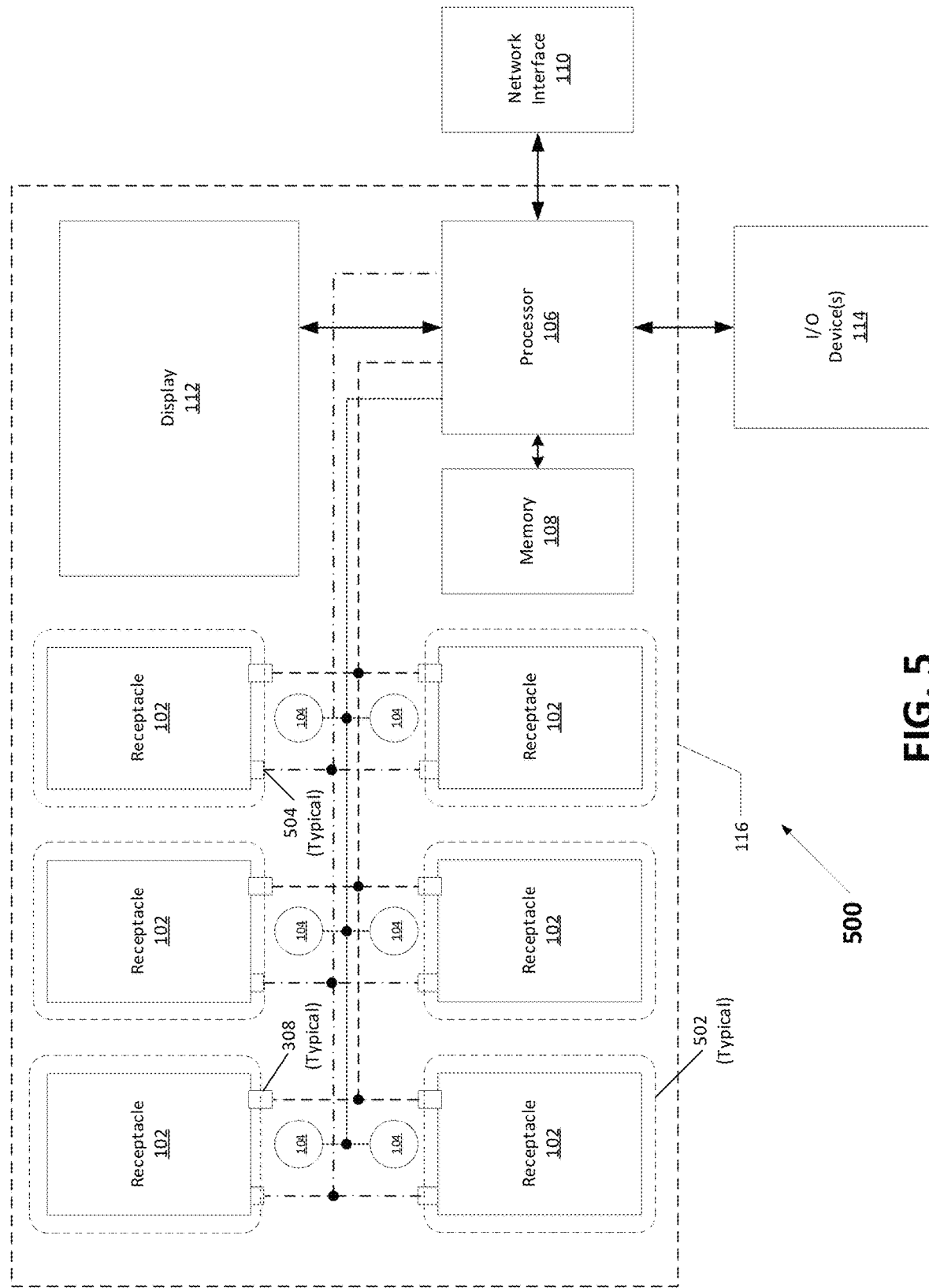
FIG. 5 illustrates a side view of an exemplary single receptacle of an embodiment of an medication management portal device.
Figure 6:
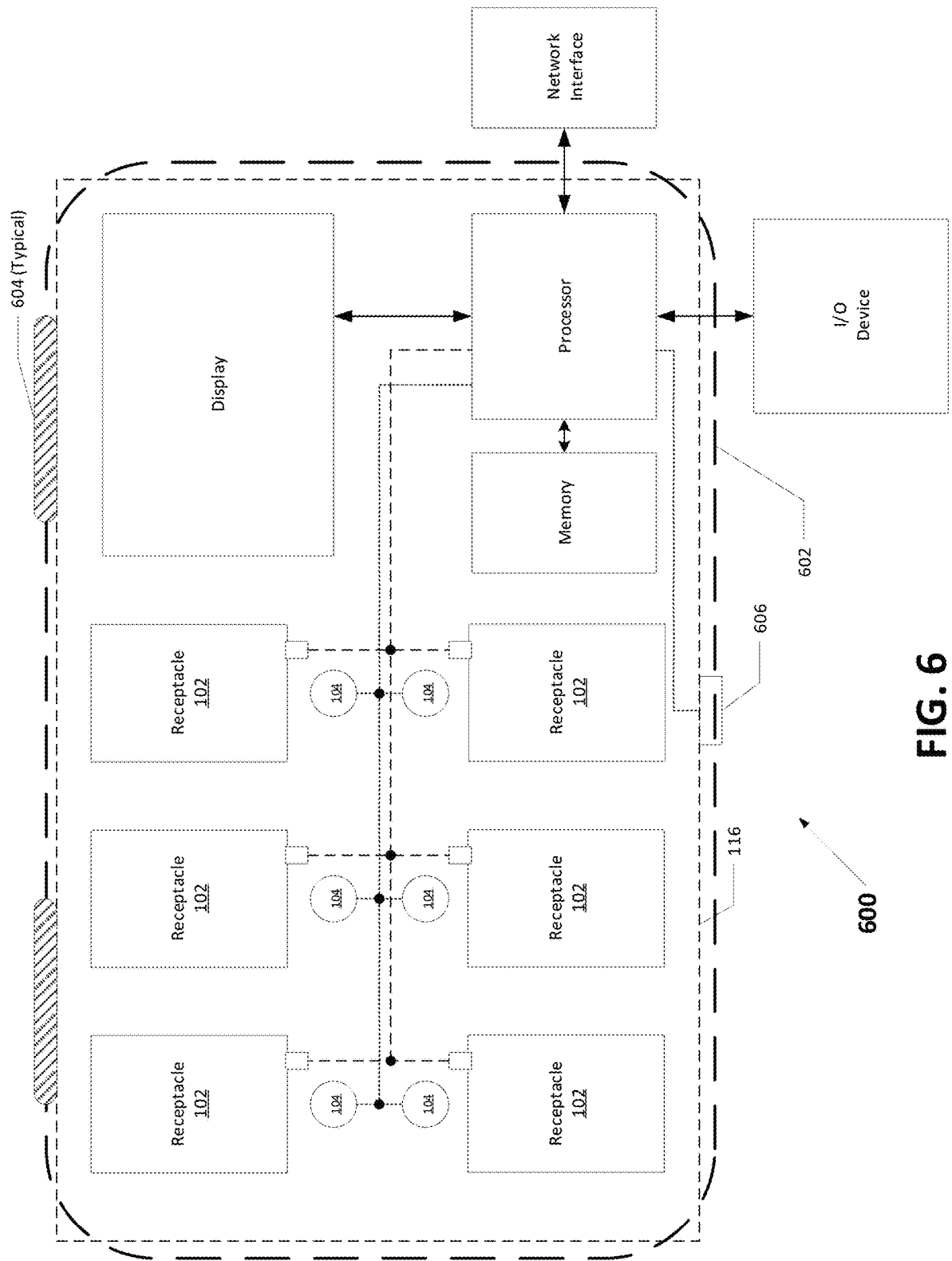
FIG. 6 illustrates yet another alternate exemplary medication management portal device.

In some embodiment, the medication management portal device may comprise a lid that covers at least one of the one or more receptacles 102. For example, FIG. 5 is an illustration of a medication management portal device 500 where each of the one or more receptacles 102 are covered by an individual lid 502. In some instances, at least a portion of the lid 502 is transparent so that the medication contained in the receptacle 102 can be seen. The lid 502 may be made of any suitable material such as metal, plastic, glass, polycarbonate, wood, etc., or combinations thereof. Typically, the lid 502 is hinged at one end or on one side. The lid may be configured such that it locks in place when opened to provide easier access to the medication in the receptacle 102. In FIG. 5, each of the receptacles 102 are associated with a sensor 308 and also a locking mechanism 504 that is in communication with the processor 106, which controls access to each receptacle 102 individually by sending signals to the locking mechanism 504 that unlocks or locks the locking mechanism 504 in accordance with computer-executable instructions executed by the processor 106. For example, the locking mechanism 504 locks the lid 502 when the medication is placed in the receptacle 102 and the medication identifier is associated with the unique receptacle identifier for the receptacle 102 that the medication is placed in. The processor 106 executes computer-executable instructions that unlock the locking mechanism 504 of the lid 502 of the receptacle 102 when it is the one or more days or times during the day that the patient is to access the medication in the receptacle 102 having the locking mechanism 504. In some instances, the processor 106 may be configured to execute computer-executable instructions to re-lock the locking mechanism 504 of the lid 502 after a period of time has elapsed once the locking mechanism 504 has been unlocked. FIG. 6 is an illustration of an alternate embodiment of a medication management portal device 600 where all of the one or more receptacles 102 are covered by a single lid 602. In this embodiment, opening the lid 602 provides access to all of the plurality of receptacles 102. As shown in FIG. 6, the lid 602 is hinged 604 along one edge of the medication management portal device 600 and has a locking mechanism 606 on the edge opposite the hinged edge. Similar to the above, the locking mechanism 602 is in communication with and controlled by the processor 106 such that the lid 602 can be locked or unlocked in accordance with instructions executed by the processor 106.

Referring back to FIGS. 2A-2G, information that may be entered into and stored in the memory 108 of the medication management portal device can include an expected time and date for retrieval of at least a portion of the medication in each of the one or more receptacles 102. When the medication in a receptacle 102 is accessed can be determined by the sensor 308 (if equipped) and/or when the lid 502, 602 is unlocked and/or opened. The processor 106 can execute computer-executable instruction that compare the recorded time and date that the at least the portion of the medication was retrieved from a receptacle 102 to an expected time and date for retrieval of at least a portion of the medication for that receptacle 102, where the expected time and date for retrieval of the at least the portion of the medication was previously stored in the memory. In some instances, if the comparison shows that the recorded time and date that the at least the portion of the medication was retrieved is not within a range that includes the expected time and date for retrieval of at least a portion of the medication or if the sensor 308 detects there was no retrieval of at least a portion of the medication within a range that includes the expected time and date for retrieval of at least a portion of the medication, the processor 106 causes an alarm to be triggered. For example, if at least one of the indicators 104 associated with each of the plurality of receptacles 102 comprises a light located proximate to the at least one receptacle 102, then the light is controlled by the processor 106 executing computer-executable instructions such that the light illuminates when the alarm is triggered. Or, if at least one of the indicators 104 associated with each of the plurality of receptacles 102 comprises a sound-emitting device located proximate to the at least one receptacle 102, then the sound-emitting device is controlled by the processor 106 executing computer-executable instructions such that the sound-emitting device emits sound when the alarm is triggered. Or, if at least one of the indicators 104 associated with each of the plurality of receptacles 102 comprises a haptic vibration device located proximate to the at least one receptacle 102, then the haptic vibration device is controlled by the processor 106 executing computer-executable instructions such that the haptic vibration device emits sound when the alarm is triggered.

As noted herein, embodiments of the medication management portal device may also comprise a display 112. In some instances, the display 112 displays information about the medication in the one of the plurality of receptacles 102 when the alarm is triggered. Also, in some embodiments, the medication management portal device is connected to a network. In some instances, the medication management portal device causes a text message to be sent to one or more devices capable of receiving text messages when the alarm is triggered. For example, the at least one of the one or more devices capable of receiving text messages may be controlled or monitored by the patient. Alternatively or optionally, the medication management portal device may cause an email message to be sent to one or more devices capable of receiving email messages when the alarm is triggered. Again, the at least one of the one or more devices capable of receiving email messages may be controlled or monitored by the patient.

Referring now to FIGS. 1 and 4-6, at least one of the indicators 104 associated with each of the plurality of receptacles 102 may comprise a light located proximate to the receptacle 102. The light can be controlled by the processor 106 executing computer-executable instructions such that the light illuminates when it is the one or more days or times during the day that the patient is to access the medication in the one of the receptacles 102. Alternatively or optionally, at least one of the indicators 104 associated with each of the plurality of receptacles 102 may comprise a sound-emitting device located proximate to the receptacle 102. The sound-emitting device can be controlled by the processor 106 executing computer-executable instructions such that the sound-emitting device emits a sound when it is the one or more days or times during the day that the patient is to access the medication in the one of the receptacles 102. Alternatively or optionally, at least one of the indicators 104 associated with each of the plurality of receptacles 102 comprises a haptic vibration device located proximate to the receptacle 102. The haptic vibration device can be controlled by the processor 106 executing computer-executable instructions such that the haptic vibration device emits a vibration when it is the one or more days or times during the day that the patient is to access the medication in the one of the receptacles 102.

In some instances, the display 112 may display information about the one of the plurality of receptacles 102 when it is the one or more days or times during the day that the patient is to access the medication in the one of the receptacles 102. Alternatively or optionally, the medication management portal device, when connected to a network (wireless or wired), may cause a text message to be sent to one or more devices capable of receiving text messages when it is the one or more days or times during the day that the patient is to access the medication in the one of the receptacles 102. In some instances at least one of the one or more devices capable of receiving text messages is controlled or monitored by the patient. Alternatively or optionally, the medication management portal device, when connected to a network, may cause an email message to be sent to one or more devices capable of receiving email messages when it is the one or more days or times during the day that the patient is to access the medication in the one of the receptacles. In some instances, at least one of the one or more devices capable of receiving text messages is controlled or monitored by the patient.

For security, compliance, and safety purposes, in some instances access to the medication management portal device is controlled by the processor 106. As used herein, "access" means having the ability to enter information into the medication management portal device, lock or unlock a lid or lids associated with receptacles 102 of the medication management portal device, access information and/or other resources over a network using the medication management portal device, and the like. For example, access to the medication management portal device may require establishing and entering a password and/or a username via the I/O device 114. In some instances, the I/O device 114 may comprise a biometric sensor in communication with the processor 106. The biometric sensor can be used to establish and enter biometric features for access to the medication management portal device. For example, the biometric sensor may comprise a fingerprint scanner and the biometric feature comprises a fingerprint of an authorized user. As another example, the biometric sensor may comprise a camera or a facial recognition scanner and the biometric features comprise facial features of an authorized user. In yet another example, the biometric sensor comprises a retina scanner and the biometric features comprise a retina of an authorized user. It is to be appreciated that these are only examples of biometric sensors that can be used with the medication management portal system and the disclosure is not to be limited to these specific examples.

Figure 7:
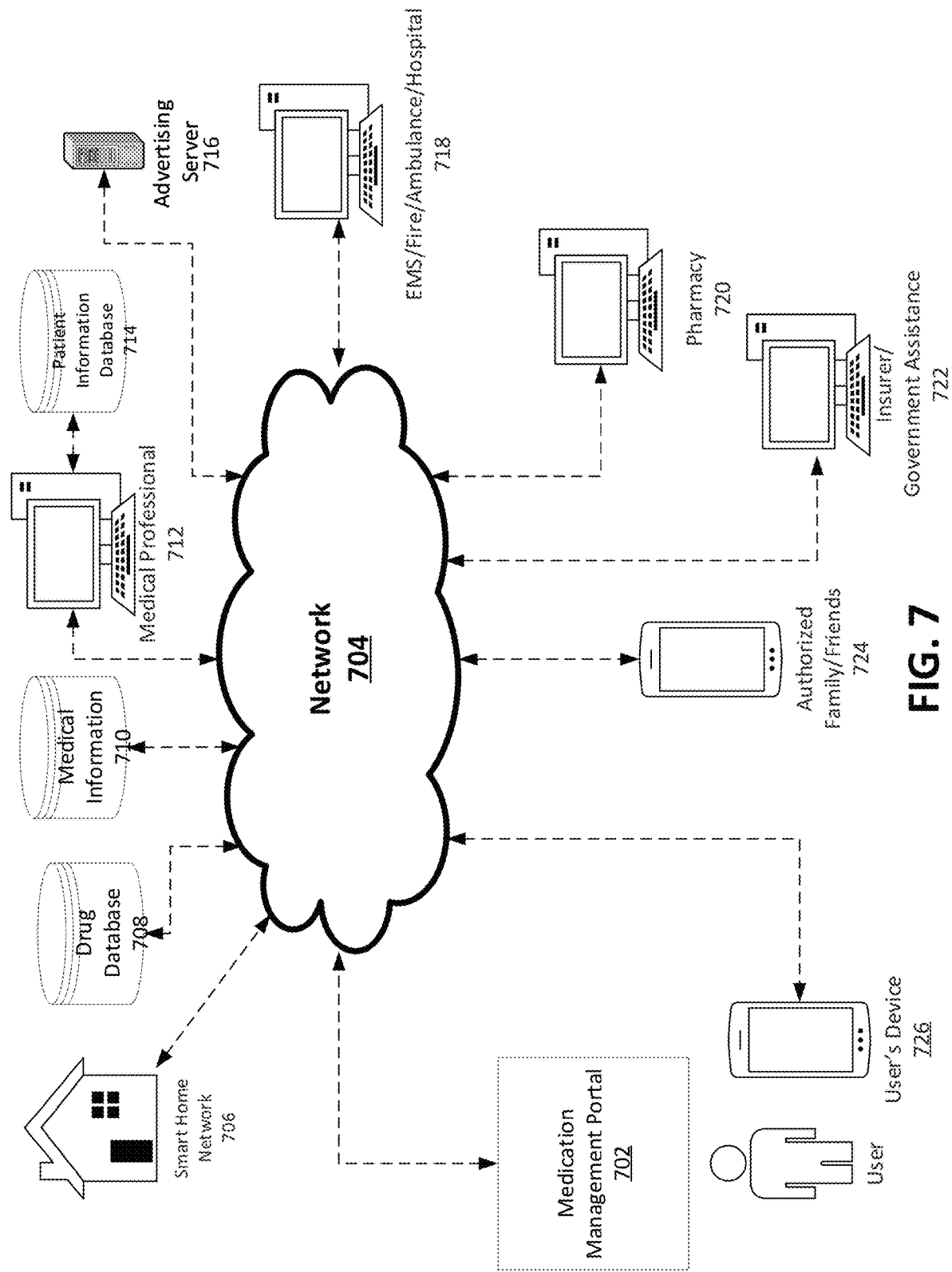
FIG. 7 illustrates an exemplary system for using an embodiment of a medication management portal device to interact with resources over a network.

As noted herein, embodiments of the medication management portal device may be connected to a network using the communications interface 110. Such a network connection allows access to information and resources, including live, two-way interaction. FIG. 7 illustrates an exemplary system for using an embodiment of a medication management portal device 702 to interact with resources over a network 704. The network 704 can be wired (including fiber optic) and/or wireless, or combinations thereof. It can be a LAN, WAN, WLAN or any other form of network and will generally provide internet access. In some instances, the network 704 is at least in part comprised of a cloud-based service. As shown in FIG. 7, connecting the medication management portal device 702 to the network 704 allows the medication management portal to access, provide and/or receive information from various and multiple resources. These resources may include, but are not limited to a smart home network 706, a drug database 708 (note that some of these resources may require the patient to be an authorized user and require additional steps (e.g., logging in) to access these resources), medical information 710, a medical professional (e.g., doctor, physician's assistant, nurse, etc.) 712 and medical information/history 714 about the patient, an advertising server 716, emergency services 718 such as EMS, fire, ambulance, hospital, etc., a pharmacy 720, insurance/government assistance 722, etc. The network 704 may also allow authorized family/friends 724 to interact with the patient and/or receive information about the patient, alerts and/or alarms, and the like through/from the medication management portal device 702 using a device such as a smart phone. The network 704 may also allow the patient/user to enter and/or receive information including alerts and/or alarms and the like through/from the medication management portal device 702 using a portable electronic device 726 that connects wirelessly to the network 704 and/or to the medication management portal device 702 (using, for example, Bluetooth). The portable electronic device may be, in some instances, a smartphone, laptop computer, iPad™ (and similar devices), and the like that wirelessly connects with the medication management portal device through the network 704 and/or directly using a secure app executing at least in part on the portable electronic device.

For example, in some instances the medication management portal device further comprises a speaker and a microphone. The speaker and the microphone enable a user of the medication management portal device to conduct a two-way audio connection with a health professional 712 over the network 704. In some instances, the medication management portal device further comprises a camera. The camera enables the user of the medication management portal device to conduct a two-way video connection with the health professional 712 over the network 704. For example, the camera can be used to monitor (real-time) and/or record a video of the user of the medication management portal device administering medication retrieved from at least one of the plurality of receptacles 102. The monitored administration of the medication or the recorded video of the user of the medication management portal device used for administering the medication from at least one of the plurality of receptacles 102 can be used to verify the user's adherence to a medication regimen. Such verification may be performed by a person (e.g., a health care professional) watching (either live or recorded) the administration of the medication, or can be verified by a separate computer system executing video analysis software.

As shown in FIG. 7, the medication management portal device 702 may be connected to an advertising server 716 through the network. The advertising server 716 can provide advertisements that are displayed on the display 112 of the medication management portal device 702. For example, the medication identifier for the medication placed in the one of the receptacles 102 can be provided to the advertising server 716 and advertisements displayed on the display 112 are selected by the advertising server 716 at least in part based on the medication identifier for the medication placed in the one of the receptacles 102.

Figure 8:
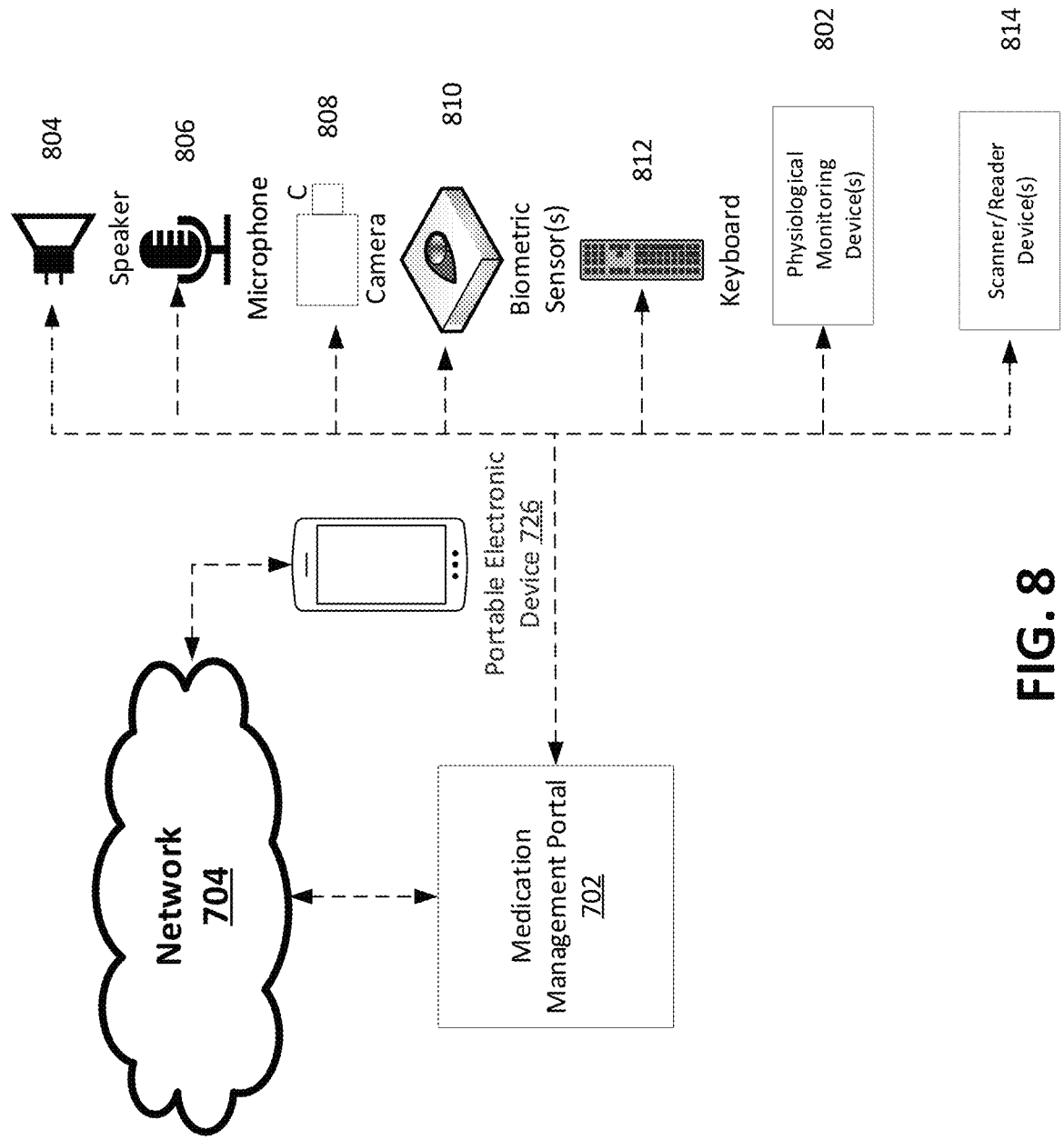
FIG. 8 illustrates an exemplary medication management portal device interfaced with a non-exhaustive list of input/output (I/O) devices.

In some instances, the medication management portal device 702 can be connected to various and several I/O devices 114 including one or more associated physiological monitoring devices 802, as shown in FIG. 8. In some instances, the one or more physiological monitoring devices 802 are used to measure one or more of ECG, respiration, heart rate, temperature, blood pressure, urinalysis, stool analysis, and the like of the patient, with the data from the one or more associated physiological monitoring devices 802 received by the medication management portal device 702. The medication management portal device 702 is communicatively coupled through the network 704 with one or more systems associated with one or more healthcare providers 712. The information regarding one or more of ECG, respiration, heart rate, temperature, blood pressure, urinalysis, stool analysis, and the like of the patient received by the medication management portal device 702 from the one or more associated physiological monitoring devices 802 is transmitted to the one or more systems associated with one or more healthcare providers 712. In return, information from the one or more healthcare providers 712 may be transmitted to the medication management portal device 702 for the patient after analyzing the data received from the one or more associated physiological monitoring devices 802. In some instances, the information from the medication management portal device 702 transmitted to the one or more systems associated with one or more healthcare providers 712 includes physiological information of a person from the one or more physiological monitoring devices 802 associated with the medication management portal device 702 that are used to measured one or more of ECG, respiration, heart rate, temperature, blood pressure urinalysis, and stool analysis information and information related to the medication identifier for the medication placed in the one of the receptacles 102. In some instances, the information transmitted from the medication management portal device 702 to the one or more systems associated with one or more healthcare providers 712 includes patient information. The patient information may include, for example, patient age, weight, race, sex, ethnicity, genotype, and the like, wherein the patient information has been entered (or received) into the medication management portal device 702 using one or more I/O devices 114. In some instances, the information from the medication management portal device 702 transmitted to the one or more systems associated with one or more healthcare providers 712 can be archived as medical information/history 714 and used for medical analyses. In some instances, the information may be anonymized prior to being archived.

Referring again to FIG. 8, which illustrates an exemplary medication management portal device 702 interfaced with a non-exhaustive list of input/output (I/O) devices 114. The exemplary I/O devices 114 may include, but are not limited to a speaker 804, a microphone 806, a camera 808, a biometric sensor 810, a keyboard 812, physiological monitoring devices 802, scanner/reader devices 814, and the like. In some instances, more than one I/O device 114 may be interfaced with the medication management portal device 702 at a single time.

Communications within the described systems can be subject to a number of security protocols. For example, communications can be encrypted and secured, such as HTTPS and SSL communications. The cloud computing architecture includes a firewall that only allows specific and secure communication on defined ports. In addition, the system can use authenticated sessions with a login with name and password for web service methods that a user using a medication management portal device (described herein) would use to gain access to read or alter their information. The login names and passwords can be stored in a secure fashion using hashing and encryption, and patient data including all data posts from the displays can be likewise encrypted and stored in a secure fashion by the cloud computing architecture.

Another security measure may include using an authenticated session that times out after a short period of inactivity and also can have a maximum length. Network servers can keep an audit trail or history log of all access to the system and all changes made to the system. In addition, third parties accessing data stored by the cloud computing architecture can be required to authenticate themselves and may also be further restricted to only access patients they already know.

That is, a consumer's privilege may require them to already know the patient's internal identifier with the system which would have already been provided by a patient initiated exchange of any identifying information with that consumer.

Figure 9:
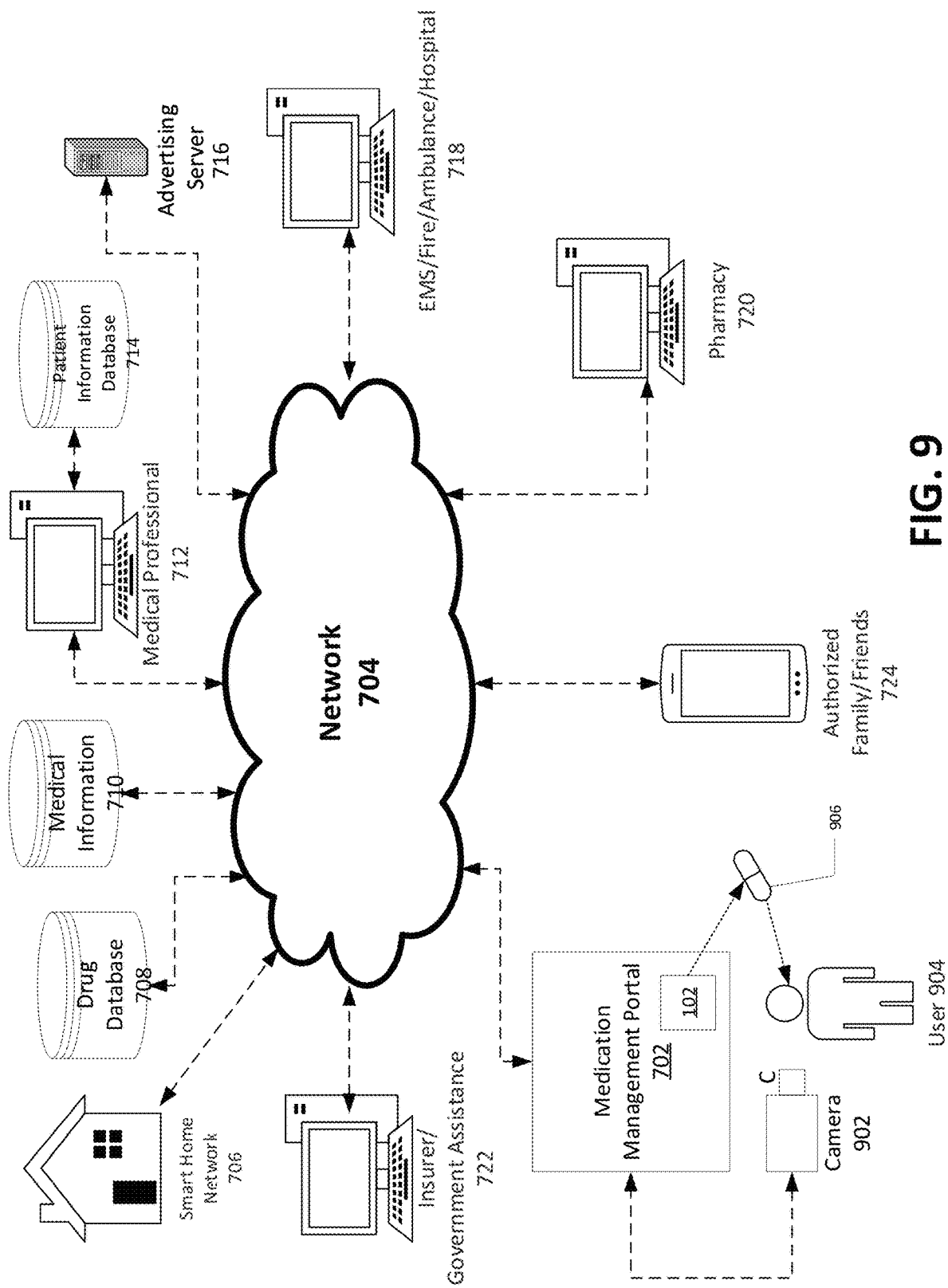
FIG. 9 illustrates an exemplary system for using an embodiment of a medication management portal device to interact with resources over a network where a user taking their prescribed medication is validated by the user being remotely monitored and/or recorded by a camera while taking the medication.

FIG. 9 is a diagrammatic representation of a system for performing a method of verifying adherence to a medication regimen using a medication management portal device 702. The method is shown in the flowchart of FIG. 10. The method comprises step 1002, providing the medication management portal device 702 that has a camera 902 in communication with the processor 106 of the medication management portal device 702. At 1004, an alert is provided by the medication management portal device 702 that it is a time for a patient 904 to receive medication 906 from one of the receptacles 102 of the medication management portal device 702. At 1006, the medication management portal device 702 provides an indication that allows the user 904 to identify the receptacle 102 that the medication is to be retrieved from. At 1008, the medication management portal device 702 causes the camera 902 to begin recording the user 904 retrieving the medication from the identified receptacle 102 and also records the user 904 or a patient using the medication from the identified receptacle 102. At 1010, video of the user 904 retrieving the medication from the identified receptacle 102 and the user 904 or the patient using the medication from the identified receptacle 102 is transmitted (real-time or delayed) over the network 704 to a device under the control of a health care professional 712. In some instances, the medication management portal device 702 further transmits over the network 704 to the device under the control of a health care professional 712 one or more of a unique identifier associated with the medication management portal device 702, a time the user retrieved the medication from the identified receptacle 102, an identification of the medication in the identified receptacle, and/or a time that the user 904 or patient used the medication from the identified receptacle 102. At 1012, the healthcare professional 712 verifies that the user's 904 or the patient' use of the medication from the identified receptacle 102 is or is not in compliance to the medication regimen. This can be done by a person watching the video and/or by machine analysis of the video.

Though not shown in FIG. 10, in some instances the device under the control of a health care professional 712 can transmit a compliance indicator over the network 704 to the medication management portal device 702 that indicates whether the user's 904 or the patient's use the medication from the identified receptacle 102 is or is not in compliance to the medication regimen. In some instances, the medication management portal device 702 provides an alert to the user 904 or the patient using the medication from the identified receptacle 102 that the use is or is not in compliance to the medication regimen. The alert can be any way of notifying a person including a sound, a light, a vibration, a message displayed ion the display 112, a text message or email sent to a device under the control of the user or patient or another authorized recipient, and the like.

FIG. 11 is a flowchart illustrating a method of medication management. The illustrated method comprises 1102, providing a medication management portal device having a plurality of medication receptacles. At 1104, the medication management portal device receives information via an I/O device for a medication that is placed in one of the receptacles, wherein the medication information may include a medication identifier for the medication placed in the one of the receptacles. In some instances, additional information about the medication placed in the one of the receptacles may be displayed on a display of the medication management portal device when the processor of the medication management portal device receives the medication identifier. In some instances, the additional information about the medication placed in the one of the receptacles has been previously stored in a memory of the medication management portal device and is retrieved from the memory by the processor using the medication identifier. In some instances, the additional information about the medication placed in the one of the receptacles is at least partially retrieved over the network by the processor using the medication identifier. In some instances, the display is used to display a plurality of medication identifiers and the medication identifier for the medication placed in the one of the receptacles is selected using the I/O device. At 1106, the medication management portal device associates the medication identifier with a unique receptacle identifier for the receptacle that the medication is placed in. At 1108, the medication management portal device receives information via the I/O device indicating one or more days or times during a day that a patient is to access the medication in the one of the receptacles. At 1110, the medication management portal device provides an indication using an indicator associated with the one of the plurality of the receptacles when it is the one or more days or times during a day that a patient is to access the medication in the one of the receptacles.

FIG. 12 is a flowchart that illustrates a method of collecting medical information using a medication management portal device. The method comprises 1202, providing a medication management portal device that includes one or more physiological monitoring devices in communication with a processor of the medication management portal device that are used to measure one or more of ECG, respiration, heart rate, temperature, blood pressure urinalysis, and stool analysis information. At step 1204, the medication management portal device transmits information from one or more of the physiological monitoring devices, the information obtained from one or more of the physiological devices is obtained at or near a time that a user retrieves a medication from one of the receptacles of the medication management portal device, over a network connected to the medication management portal device to a device configured to store information. At 1206, the medication management portal device transmits over the network to the device configured to store information, a medication identifier for the medication that the user retrieved from the one of the receptacles of the medication management portal device. At 1208, the medication management portal device transmits over the network to the device configured to store information, patient information that is entered into the medication management portal device using the I/O device, wherein the patient information includes one or more of age, weight, race, sex, ethnicity, and genotype. At 1210, the information from one or more of the physiological monitoring devices, the medication identifier for the medication that the user retrieved from the one of the receptacles of the medication management portal device, and the patient information is associated and archived in the device configured to store information. In some instances, the medication identifier for the medication that the user retrieved from the one of the receptacles of the medication management portal device, and the patient information is anonymized prior to being archived. At 1212, the stored information is used for medical analyses and/or studies.

Figure 13:
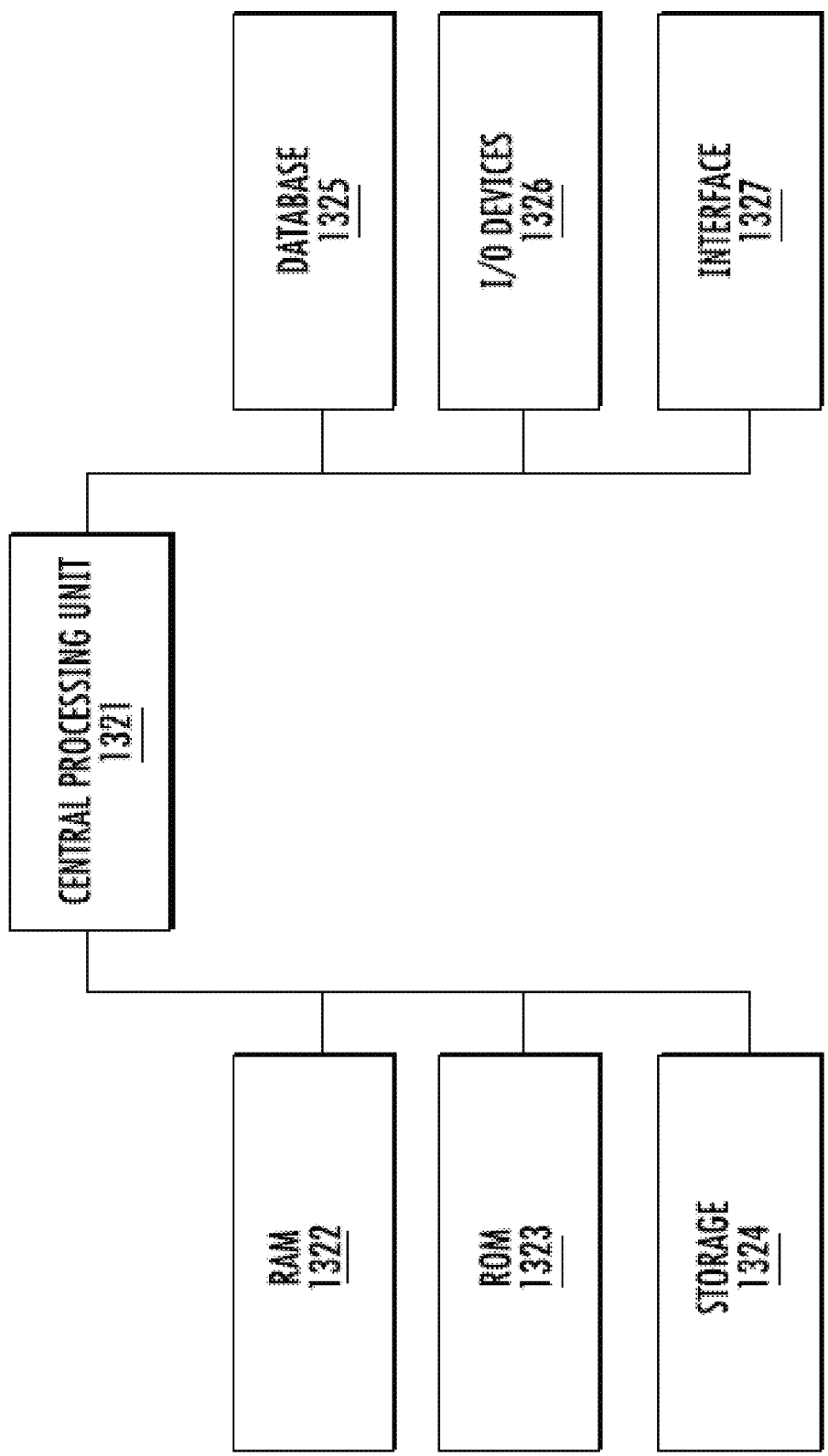
FIG. 13 illustrates an exemplary computer for use with the disclosed embodiments.

FIG. 13 illustrates an exemplary computer. Medication management portal device, the network 704 and any associated cloud computing architecture and servers, as well as other system components, can include all or some of the components shown in FIG. 13.

The computers may include one or more hardware components such as, for example, a central processing unit (CPU) 1321, a random access memory (RAM) module 1322, a read-only memory (ROM) module 1323, a storage 1224, a database 1325, one or more input/output (I/O) devices 1326, and an interface 1327. Alternatively and/or additionally, the computer may include one or more software components such as, for example, a computer-readable medium including computer executable instructions for performing a method or methods associated with the exemplary embodiments. It is contemplated that one or more of the hardware components listed above may be implemented using software. For example, storage 1324 may include a software partition associated with one or more other hardware components. It is understood that the components listed above are exemplary only and not intended to be limiting.

CPU 1321 may include one or more processors, each configured to execute instructions and process data to perform one or more functions associated with a computer for monitoring glucose levels. CPU 1321 may be communicatively coupled to RAM 1322, ROM 1323, storage 1224, database 1325, I/O devices 1326, and interface 1327. CPU 1321 may be configured to execute sequences of computer program instructions to perform various processes. The computer program instructions may be loaded into RAM 1322 for execution by CPU 1321.

RAM 1322 and ROM 1323 may each include one or more devices for storing information associated with operation of CPU 1321. For example, ROM 1323 may include a memory device configured to access and store information associated with controller 1220, including information for identifying, initializing, and monitoring the operation of one or more components and subsystems. RAM 1322 may include a memory device for storing data associated with one or more operations of CPU 1321. For example, ROM 1323 may load instructions into RAM 1322 for execution by CPU 1321.

Storage 1324 may include any type of mass storage device configured to store information that CPU 1321 may need to perform processes consistent with the disclosed embodiments. For example, storage 1324 may include one or more magnetic and/or optical disk devices, such as hard drives, CD-ROMs, DVD-ROMs, or any other type of mass media device.

Database 1325 may include one or more software and/or hardware components that cooperate to store, organize, sort, filter, and/or arrange data used by CPU 1321. For example, database 1325 may data relating to medication information, medication identifiers, dates and times that a patient is to take a medication, patient information, information about retrieval of medication from a receptacle of the medication management portal device, and the like. It is contemplated that database 1325 may store additional and/or different information than that listed above.

I/O devices 1326 may include one or more components configured to communicate information with a user associated with controller 1220. For example, I/O devices may include a console with an integrated keyboard and mouse to allow a user to maintain a database of images, update associations, and access digital content. I/O devices 1326 may also include a display including a graphical user interface (GUI) for outputting information on a monitor or display. I/O devices 1326 may also include peripheral devices such as, for example, a printer for printing information associated with controller 1220, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 1327 may include one or more components configured to transmit and receive data via a communication network, such as the Internet, a local area network, a workstation peer-to-peer network, a direct link network, a wireless network, or any other suitable communication platform. For example, interface 1327 may include one or more modulators, demodulators, multiplexers, demultiplexers, network communication devices, wireless devices, antennas, modems, and any other type of device configured to enable data communication via a communication network.

Any combination of one or more computer readable medium(s) may be utilized. The computer readable medium may be a computer readable signal medium or a computer readable storage medium. A computer readable storage medium may be, for example, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. Program code embodied on a computer readable medium may be transmitted using any appropriate medium, including but not limited to wireless, wireline, optical fiber cable, RF, etc., or any suitable combination of the foregoing.

Computer program code for may be written in any combination of one or more programming languages, including an object oriented programming language such as Java, Smalltalk, C++, or the like, and conventional procedural programming languages, such as the "C" programming language or similar programming languages. The program code may execute entirely on the computing unit.

It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

While this specification contains many specific implementation details, these should not be construed as limitations on the claims. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein. It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

The invention claimed is:

1. A medication management system comprised of: a plurality of receptacles, each receptacle comprising a lid, a bottom and one or more walls, wherein each receptacle is configured to receive and hold a medication which cannot be accessed from outside the receptacle until the lid is opened;
   a plurality of indicators, wherein each receptacle of the plurality of receptacles is associated with a corresponding one indicator of the plurality of indicators, and wherein the receptacle is separate from but proximate to the corresponding one indicator;
   a processor communicatively coupled to each of the indicators;
   a memory in communication with the processor;
   a communications interface coupled with the processor for connecting the medication management system to a network, wherein the network is connected to a wireless cellular phone system such that a user can interface remotely with the processor of the medication management system using a smartphone, wherein the smartphone includes a smartphone display that displays one or more graphical user interfaces (GUIs) on the smartphone display that are used to access, retrieve and display data from the processor of the medication management system and to enter data into the processor of the medication management system including demographic information, a medication schedule in a calendar format, entering information about a new medication, obtaining and displaying compliance information on a medication;
   a display in communication with the processor;
   an input-output (I/O) device in communication with the processor, wherein the processor executes computer-executable instructions to track dates and time, and wherein the processor further executes computer-executable instructions that cause the processor to:
      individually identify each of the plurality of receptacles, wherein each of the plurality of receptacles has a unique receptacle identifier;
      receive information via the I/O device and/or the smartphone if a medication is placed in one of the receptacles;
      receive a medication identifier for the medication placed in the one of the receptacles;
      associate the medication identifier with the unique receptacle identifier for the receptacle that the medication is placed in;
      receive information via the I/O device and/or the smartphone indicating one or more days or times during a day that a patient is to access the medication in the one of the receptacles; and
      provide an indication using the corresponding indicator associated with the one of the plurality of the receptacles at the one or more days or times during a day that a patient is to access the medication in the one of the receptacles.

2. The system of claim 1, wherein the medication identifier is input into the system using the I/O device and/or the smartphone.

3. The system of claim 1, wherein each of the plurality of receptacles is configured to hold a medication in a pill form, a liquid form, or in a pre-packaged tear-off strip or roll form.

4. The system of claim 1, wherein the receptacle further comprises a lock that is controlled by the processor, wherein the lock locks the lid when the medication is placed in the receptacle and the medication identifier is associated with the unique receptacle identifier for the receptacle that the medication is placed in.

5. The system of claim 1, wherein at least one of the plurality of receptacles includes a sensor that detects a presence or absence of an object in the at least one receptacle.

6. The system of claim 5, wherein the sensor detects retrieval of at least a portion of the medication in the at least one receptacle.

7. The system of claim 6, wherein the processor records a time and date that the at least the portion of the medication was retrieved.

8. The system of claim 7, wherein the processor compares the recorded time and date that the at least the portion of the medication was retrieved to an expected time and date for retrieval of at least a portion of the medication, wherein the expected time and date for retrieval of the at least the portion of the medication is previously stored in the memory.

9. The system of claim 8, wherein if the comparison shows that the recorded time and date that the at least the portion of the medication was retrieved is not within a range that includes the expected time and date for retrieval of at least a portion of the medication or if the sensor detects there was no retrieval of at least a portion of the medication within a range that includes the expected time and date for retrieval of at least a portion of the medication, the processor causes an alarm to be triggered.

10. The system of claim 9, wherein the display displays information about the medication in the one of the plurality of receptacles when the alarm is triggered and/or causes a text message or an email to be sent to one or more devices capable of receiving text messages and/or emails when the alarm is triggered.

11. The system of claim 1, wherein at least one of the indicators associated with each of the plurality of receptacles comprises a light located proximate to the receptacle, wherein the light is controlled by the processor executing computer-executable instructions such that the light illuminates at the one or more days or times during the day that the patient is to access the medication in the one of the receptacles, or wherein at least one of the indicators associated with each of the plurality of receptacles comprises a sound-emitting device located proximate to the receptacle, wherein the sound-emitting device is controlled by the processor executing computer-executable instructions such that the sound-emitting device emits a sound at the one or more days or times during the day that the patient is to access the medication in the one of the receptacles.

12. The system of claim 1, wherein the system further comprises a speaker and a microphone, wherein the speaker and the microphone enable a user of the medication management system to conduct a two-way audio connection with a health professional over the network.

13. The system of claim 12, wherein the system further comprises a camera, wherein the camera enables the user of the medication management system to conduct a two-way video connection with the health professional.

14. The system of claim 13, wherein the camera records a video of the user of the medication management system administering the medication from at least one of the plurality of receptacles.

15. The system of claim 14, wherein the recorded video of the user of the medication management system administering the medication from at least one of the plurality of receptacles is used to verify the user's adherence to a medication regimen.

16. The system of any one of claim 1, wherein the medication management system is communicatively coupled through the network with one or more systems associated with one or more healthcare providers, wherein information from the medication management system is transmitted to the one or more systems associated with one or more healthcare providers and wherein information from the one or more healthcare providers is transmitted to the medication management system.

17. The system of claim 16, wherein the information from the medication management system transmitted to the one or more systems associated with one or more healthcare providers includes physiological information of a person from one or more physiological monitoring devices associated with the medication management system that are used to measured one or more of ECG, respiration, heart rate, temperature, blood pressure urinalysis, and stool analysis information and information related to the medication identifier for the medication placed in the one of the receptacles.

18. The system of claim 17, wherein the information from the medication management system transmitted to the one or more systems associated with one or more healthcare providers is archived and used for medical analyses.

19. The system of claim 16, wherein the information from the medication management system transmitted to the one or more systems associated with one or more healthcare providers includes patient information.

20. The system of claim 19, wherein the patient information is entered into the medication management system using the I/O device and/or the smartphone and the patient information include age, weight, race, sex, ethnicity, and genotype.

21. The system of claim 1, wherein the network is connected to an advertising server, wherein advertisements are displayed on the display.

22. The system of claim 21, wherein the medication identifier for the medication placed in the one of the receptacles is provided to the advertisement server and advertisements displayed on the display are selected by the advertising server at least in part based on the medication identifier for the medication placed in the one of the receptacles.

23. A method of medication management comprising:
providing a medication management device, wherein the medication management device is comprised of:
a plurality of receptacles, each receptacle comprising a lid, a bottom and one or more walls, wherein each receptacle is configured to receive and hold a medication which cannot be accessed from outside the receptacle until the lid is opened;
a plurality of indicators, wherein each receptacle of the plurality of receptacles is associated with a corresponding one indicator of the plurality of indicators, and wherein the receptacle is separate from but proximate to the corresponding one indicator;
a processor communicatively coupled to each of the indicators, wherein the processor executes computer-executable instructions to track dates and time, and wherein the processor further executes computer-executable instructions that cause the processor to individually identify each of the plurality of receptacles, wherein each of the plurality of receptacles has a unique receptacle identifier;
a memory in communication with the processor;

a communications interface coupled with the processor for connecting the medication management device to a network;
a display in communication with the processor; and
an input-output (I/O) device in communication with the processor, wherein the network is connected to a wireless cellular phone system such that a user can interface remotely with the processor of the medication management device using a smartphone, wherein the smartphone includes a smartphone display that displays one or more graphical user interfaces (GUIs) on the smartphone display that are used to access, retrieve and display data from the processor of the medication management device and to enter data into the processor of the medication management device including demographic information, a medication schedule in a calendar format, entering information about a new medication, obtaining and displaying compliance information on a medication;

receiving, by the medication management device, information via the I/O device and/or the smartphone for a medication that is placed in one of the receptacles;

receiving, by the medication management device, a medication identifier for the medication placed in the one of the receptacles;

associating, by the medication management device, the medication identifier with the unique receptacle identifier for the receptacle that the medication is placed in;

receiving, by the medication management device, information via the I/O device and/or the smartphone indicating one or more days or times during a day that a patient is to access the medication in the one of the receptacles; and providing, by the medication management device, an indication using the indicator associated with the one of the plurality of the receptacles and/or via the smartphone at the one or more days or times during a day that a patient is to access the medication in the one of the receptacles.

24. A method of verifying adherence to a medication regimen using a medication management device, said method comprising:
providing a medication management device, wherein the medication management device is comprised of:
a plurality of receptacles, each receptacle comprising a lid, a bottom and one or more walls, wherein each receptacle is configured to receive and hold a medication which cannot be accessed from outside the receptacle until the lid is opened;
a plurality of indicators, wherein each receptacle of the plurality of receptacles is associated with a corresponding one indicator of the plurality of indicators, and wherein the receptacle is separate from but proximate to the corresponding one indicator;
a processor communicatively coupled to each of the indicators, wherein the processor executes computer-executable instructions to track dates and time, and wherein the processor further executes computer-executable instructions that cause the processor to individually identify each of the plurality of receptacles, wherein each of the plurality of receptacles has a unique receptacle identifier;
a memory in communication with the processor;
a communications interface coupled with the processor that connects the medication management device to a network,
wherein the network is connected to a wireless cellular phone system such that a user can interface remotely with the processor of the medication management device using a smartphone, wherein the smartphone includes a smartphone display that displays one or more graphical user interfaces (GUIs) on the smartphone display that are used to access, retrieve and display data from the processor of the medication management device and to enter data into the processor of the medication management device including demographic information, a medication schedule in a calendar format, entering information about a new medication, obtaining and displaying compliance information on a medication;
a display in communication with the processor;
an input-output (I/O) device in communication with the processor; and
a camera in communication with the processor;
providing, by the medication management device, an alert at a time for a patient to receive medication from one of the receptacles of the medication management device;
providing, by the medication management device, an indication that allows the user to identify the receptacle that the medication is to be retrieved from;
recording, by the medication management device, using the camera, a user retrieving the medication from the identified receptacle;
recording, by the medication management device, using the camera, the user or a patient using the medication from the identified receptacle; and
transmitting, by the medication management device, a video of the user retrieving the medication from the identified receptacle and the user or the patient using the medication from the identified receptacle, wherein the video is transmitted over the network to a device under the control of a health care professional.

25. A method of collecting medical information using a medication management device, said method comprising:
providing a medication management device, wherein the medication management device is comprised of:
a plurality of receptacles, each receptacle comprising a lid, a bottom and one or more walls, wherein each receptacle is configured to receive and hold a medication which cannot be accessed from outside the receptacle until the lid is opened;
a plurality of indicators, wherein each receptacle of the plurality of receptacles is associated with a corresponding one indicator of the plurality of indicators, and wherein the receptacle is separate from but proximate to the corresponding one indicator;
a processor communicatively coupled to each of the indicators, wherein the processor executes computer-executable instructions to track dates and time, and wherein the processor further executes computer-executable instructions that cause the processor to individually identify each of the plurality of receptacles, wherein each of the plurality of receptacles has a unique receptacle identifier;
a memory in communication with the processor;
a communications interface coupled with the processor that connects the medication management device to a network, wherein the network is connected to a wireless cellular phone system such that a user can interface remotely with the processor of the medication management device using a smartphone, wherein the smartphone includes a smartphone display that displays one or more graphical user interfaces (GUIs) on the smartphone display that are used to access, retrieve and display data from the processor of the medication management device and to enter data into the processor of the medication management device including demographic information, a medication schedule in a calendar format, entering information about a new medication, obtaining and displaying compliance information on a medication;

a display in communication with the processor;

an input-output (I/O) device in communication with the processor; and one or more physiological monitoring devices that are used to measure one or more of ECG, respiration, heart rate, temperature, blood pressure urinalysis, and stool analysis information in communication with the processor;

transmitting, by the medication management device, information from one or more of the physiological monitoring devices, wherein the information from one or more of the physiological devices is obtained at or near a time that a user retrieves a medication from one of the receptacles of the medication management device, wherein the information is transmitted over the network to a device configured to store information;

transmitting, by the medication management device, over the network to the device configured to store information, a medication identifier for the medication that the user retrieved from the one of the receptacles of the medication management device; and transmitting, by the medication management device, over the network to the device configured to store information, patient information that is entered into the medication management device using the I/O device and/or the smartphone, wherein the patient information includes one or more of age, weight, race, sex, ethnicity, and genotype.

* * * * *